(12) United States Patent
Sokol et al.

(10) Patent No.: US 9,857,288 B2
(45) Date of Patent: Jan. 2, 2018

(54) LASER BOND INSPECTION WITH COMPACT SURFACE MOTION SENSOR

(71) Applicants: David Sokol, Dublin, OH (US); Craig Walters, Powell, OH (US)

(72) Inventors: David Sokol, Dublin, OH (US); Craig Walters, Powell, OH (US)

(73) Assignee: LSP TECHNOLOGIES, INC., Dublin, OH (US)

(*) Notice: Subject to any disclaimer, the term of this patent is extended or adjusted under 35 U.S.C. 154(b) by 147 days.

(21) Appl. No.: 14/530,745

(22) Filed: Nov. 1, 2014

(65) Prior Publication Data

US 2015/0122046 A1 May 7, 2015

Related U.S. Application Data

(60) Provisional application No. 61/898,998, filed on Nov. 1, 2013.

(51) Int. Cl.
| | |
|---|---|
| *G01B 11/00* | (2006.01) |
| *G01N 19/04* | (2006.01) |
| *G01N 29/24* | (2006.01) |
| *G01L 1/24* | (2006.01) |
| *G01B 11/16* | (2006.01) |
| *G01N 3/06* | (2006.01) |

(52) U.S. Cl.
CPC ......... *G01N 19/04* (2013.01); *G01N 29/2412* (2013.01); *G01N 29/2418* (2013.01); *G01B 11/16* (2013.01); *G01B 11/18* (2013.01); *G01L 1/24* (2013.01); *G01L 1/242* (2013.01); *G01N 3/068* (2013.01); *G01N 2203/005* (2013.01); *G01N 2203/0055* (2013.01)

(58) Field of Classification Search
CPC ....................................................... G01B 11/16
USPC .............................................................. 73/800
See application file for complete search history.

(56) References Cited

U.S. PATENT DOCUMENTS

| | | | |
|---|---|---|---|
| 4,004,456 A | 1/1977 | Vahaviolos | |
| 4,901,357 A * | 2/1990 | Albright | ............... H02K 33/16 381/396 |
| 5,473,315 A | 12/1995 | Holroyd | |
| 6,008,887 A | 12/1999 | Klein et al. | |
| 6,263,737 B1 | 7/2001 | Schoess | |
| 6,282,964 B1 * | 9/2001 | Hancock | ............... G01M 3/24 73/622 |
| 6,512,584 B1 | 1/2003 | O'Loughlin et al. | |
| 6,554,921 B2 | 4/2003 | Sokol et al. | |
| 6,848,321 B2 * | 2/2005 | Bossi | ............... G01N 3/00 73/788 |

(Continued)

FOREIGN PATENT DOCUMENTS

| | | | |
|---|---|---|---|
| GB | 2225427 | * 11/1988 | ............. G01N 29/04 |
| GB | 2225427 A | 5/1990 | |

OTHER PUBLICATIONS

Ehrhart, Bastien, Methods for the Quality Assessment of Adhesive Bonded CFRP Structures—A Resume, NDT in Aerospace 2010, pp. 1-9.*

(Continued)

*Primary Examiner* — Clayton E LaBalle
*Assistant Examiner* — Kevin Butler
(74) *Attorney, Agent, or Firm* — Benesch, Friedlander, Coplan & Aronoff LLP

(57) ABSTRACT

Methods, systems, and apparatuses are disclosed for laser bond inspection of an angled or compact bonded article.

18 Claims, 6 Drawing Sheets

(56) References Cited

U.S. PATENT DOCUMENTS

| | | | |
|---|---|---|---|
| 7,253,908 B2 | 8/2007 | Vaccaro et al. | |
| 7,270,004 B2 | 9/2007 | Dickinson et al. | |
| 7,509,876 B1 * | 3/2009 | Sokol | G01N 19/04 73/150 A |
| 7,735,377 B1 | 6/2010 | Sokol et al. | |
| 7,770,454 B2 * | 8/2010 | Sokol | G01N 29/2412 73/588 |
| 7,775,122 B1 | 8/2010 | Toller et al. | |
| 8,156,811 B2 * | 4/2012 | Toller | G01N 29/043 73/588 |
| 8,225,664 B1 * | 7/2012 | Sokol | G01N 29/041 73/588 |
| 9,201,017 B2 | 12/2015 | Lahrman et al. | |
| 2015/0122046 A1 * | 5/2015 | Sokol | G01N 29/2418 73/800 |
| 2015/0128717 A1 * | 5/2015 | May | B23K 26/009 73/800 |
| 2016/0054216 A1 * | 2/2016 | Sokol | G01N 19/04 73/800 |

OTHER PUBLICATIONS

R.D. Adams, and P. Cawley, "A Review of Defect types and Nondestructive Testing Techniques for Compoosites and Bonded Joints," NDT International, Aug. 1988, pp. 208-222.*

R. Bossi, K. Housen and C. Walters, "Laser Bond Inspection Device for Composites: Has the Holy Grail Been Found?" Nondestructive Testing Information Analysis Center, vol. 30, No. 2. 2005.

R. D. Adams, and P. Cawley, "A Review of Defect types and Nondestructive Testing Techniques for Composites and Bonded Joints," NDT International, Aug. 1988, pp. 208-222.

* cited by examiner

LASER BOND INSPECTION WITH COMPACT SURFACE MOTION SENSOR

This application claims priority from U.S. Provisional Patent Application No. 61/898,998, filed on Nov. 1, 2013, which is incorporated by reference herein in its entirety.

BACKGROUND

Bonded materials are used in a variety of structural applications. For example, adhesively bonded, laminated composite structures are increasingly being used in aircraft construction to reduce weight, reduce or eliminate the number of separate components, and improve fuel efficiency. The presence of material defects in a composite aircraft structure can lead to disastrous failure of the structure under flight loads. These defects may exist in the composite laminate itself, as well as in the adhesive bonds in the structure. The defects may arise as a result of damage during service, or in the original manufacturing process.

The growing ubiquity of composite structures has led to an increased need for techniques to evaluate the strength of the composite structures, including the adhesive bonds themselves, without damaging or destroying the composite structures. Conventional nondestructive evaluation ("NDE") techniques are useful when a gap, crack, or void is present in a bonded material. However, conventional NDE techniques do not adequately identify deficiencies, such as weak bonds or "kissing bonds," where materials bonded together are in contact but without adequate structural strength. These deficiencies can result from bond surface contamination, improperly mixed or outdated adhesives, and improper adhesive application.

Laser bond inspection ("LBI") is an NDE technique for testing the integrity of bonded materials and structures. LBI is a method that involves sending a precisely controlled dynamic stress wave through an adhesive bond of a composite structure. Generally speaking, and with reference to FIG. 1, LBI 100 involves the deposition of laser energy 102 at a first surface 106 of a bonded material 104, generating a compressive stress wave 108. A first laser pulse 102 is applied to first surface 106 of bonded composite structure 104 with an opaque overlay 112 and a transparent (tamping) overlay 110 applied to surface 106. Laser pulse 102 passes through transparent overlay 110 and is absorbed by opaque overlay 112. A plasma is created and as the plasma blows off, compressive stress wave 108 is induced into surface 106. Generally speaking, no intentional heating occurs in the composite structure, and surface damage is attempted to be avoided. The shape of stress wave 108 can be tailored to several hundreds of nanoseconds in duration. The magnitude of stress wave 108 is a function of the laser input irradiance, which facilitates generation of calibrated stress waves. Compressive stress wave 108 propagates through bonded material 104, through a bond of interest 114, to a second surface 116 of bonded material 104, where stress wave 108 is reflected as a tensile wave (not shown). The tensile wave propagates back through bonded material 104 and, when it reaches bond 114, stresses bond 114. The application of dynamic stress on bonded material 104 is selected to be low enough to have little or no effect on the integrity of bonded material 104 or bond 114 if bond 114 is sufficiently strong. However, if bond 114 is below a suitable strength, the tensile wave will cause bond 114 to fail (or will expose its non-bonded nature, in the case of a kissing bond).

By observing changes in the front surface or back surface motion, a determination can be made on the strength and reliability of the bond. Various sensing means exist for observing changes in the surface motion. U.S. Pat. No. 6,848,321 (The Boeing Company), which is incorporated by reference herein in its entirety, teaches the use of Velocity Interferometer System for Any Reflector (VISAR) probes for capturing surface velocity. U.S. Pat. Nos. 7,770,454 and 8,156,811 (LSP Technologies, Inc.), both of which are incorporated herein by reference in their entireties, teach LBI systems using VISAR probes, electromagnetic acoustic transducer (EMAT) coils, capacitance probes, and piezoelectric ultrasonic transducers (UT) as sensors. While various LBI systems employing sensing means exists for measuring surface motion, the LBI systems disclosed herein provide additional advantages in evaluating bonds in angled structures and confined spaces.

SUMMARY

Systems and methods are provided to inspect and evaluate a bond line in confined composite structures and/or composite structures with angled walls (up to 50° with respect to normal to the part surface) formed by pi joints.

In one embodiment, a system for laser bond inspection of a bond in a compact and/or angled bonded article is provided, the system comprising: (1) a laser configured to produce a pulsed laser beam; (2) a laser beam delivery system operable to deliver the pulsed laser beam from the laser to an inspection head; (3) an inspection head, the inspection head configured to deliver the pulsed laser beam to the bonded article; and (4) a compact surface motion sensor, operable to detect surface motion after laser interrogation of the bonded in the bonded article and to produce one or more signals in response to detecting the surface motion.

In another embodiment, a system for laser bond inspection of a bond in a compact and/or angled bonded article is provided, the system comprising: (1) a laser, the laser configured to generate laser beam pulses having: a pulse energy between about 3-50 Joules per pulse; a 70-300 ns pulse width; and a 5-12 mm beam diameter at a surface of the bonded article, the laser further configured to generate the laser beam pulses in a low-high-low pulse energy sequence to produce stress waves through the bond of the bonded article; (2) a laser beam delivery system comprising at least one of: one or more mirrors; an optical fiber; and an articulated arm operatively connected to an inspection head; the laser beam delivery system operable to deliver the laser beam pulses generated by the laser to an inspection head; (3) an inspection head, the inspection head operable to be angled at up to about 50 degrees with respect to normal to a bonded article surface, the inspection head further comprising at least one of: a first output operable to generate a transparent overlay; a second output operable to output the laser beam pulses; an attachment area operable to fixedly attach the inspection head to the bonded article surface; and a compact surface motion sensor area operable to hold one or more compact surface motion sensors on the inspection head; (4) a compact surface motion sensor, the compact surface motion sensor comprising at least one of: one or more off-axis EMATs operatively connected to the inspection head for detecting surface motion at a location off-axis from a laser beam impact area; an optical interferometer operable with a fiber delivered low energy continuous wave laser to detect surface motion; the compact surface motion sensor further operable to produce a signal in response to detecting surface motion.

In another embodiment, a method for non-destructive testing of a bond in a compact and/or bonded article, the method comprising: lasing a bonded article with a pulsed laser beam in a low-high-low pulse energy sequence, each pulse having a pulse energy of between about 3 J and about 50 J; and detecting surface motion at a location off-axis from a laser beam impact area on the bonded article using one or more compact surface motion sensors.

BRIEF DESCRIPTION OF THE DRAWINGS

The accompanying figures, which are incorporated in and constitute a part of the specification, illustrate various example systems, methods, and results, and are used merely to illustrate various example embodiments.

DETAILED DESCRIPTION

Figure 1:
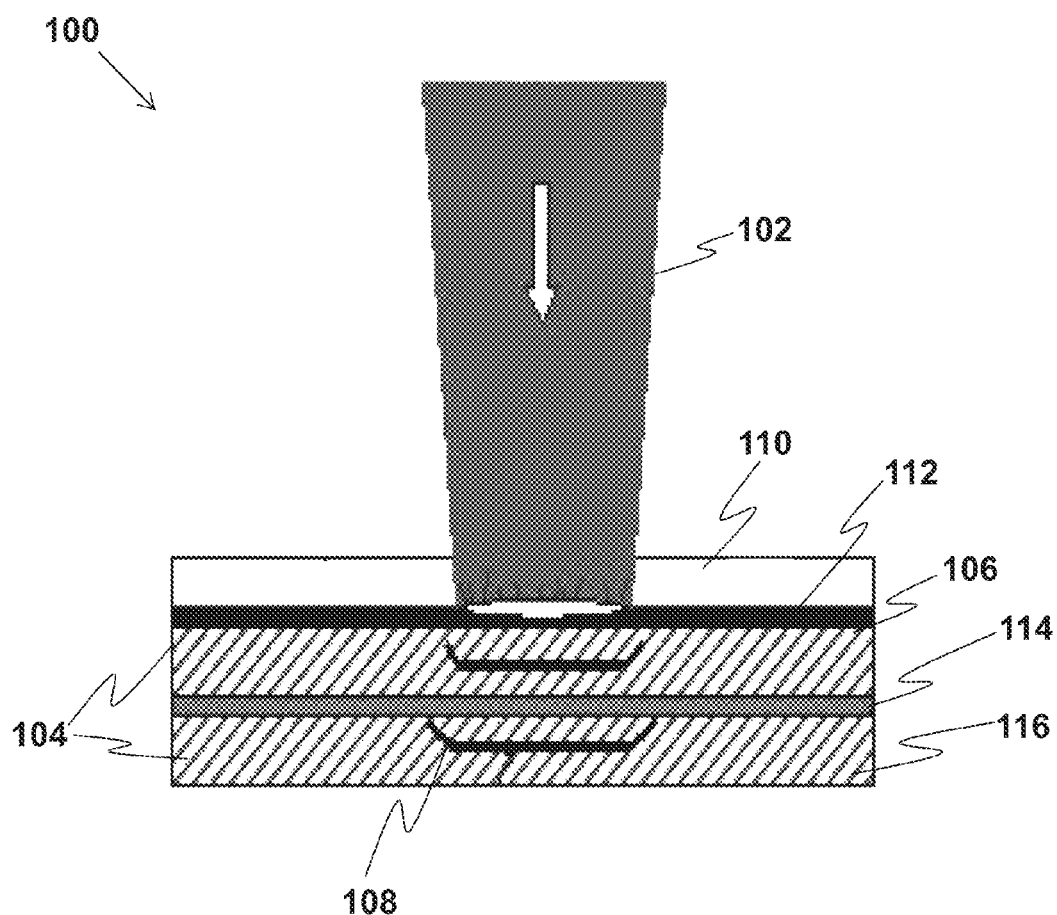
FIG. 1 illustrates a schematic of the initiation of the laser bond inspection process.
Figure 2:
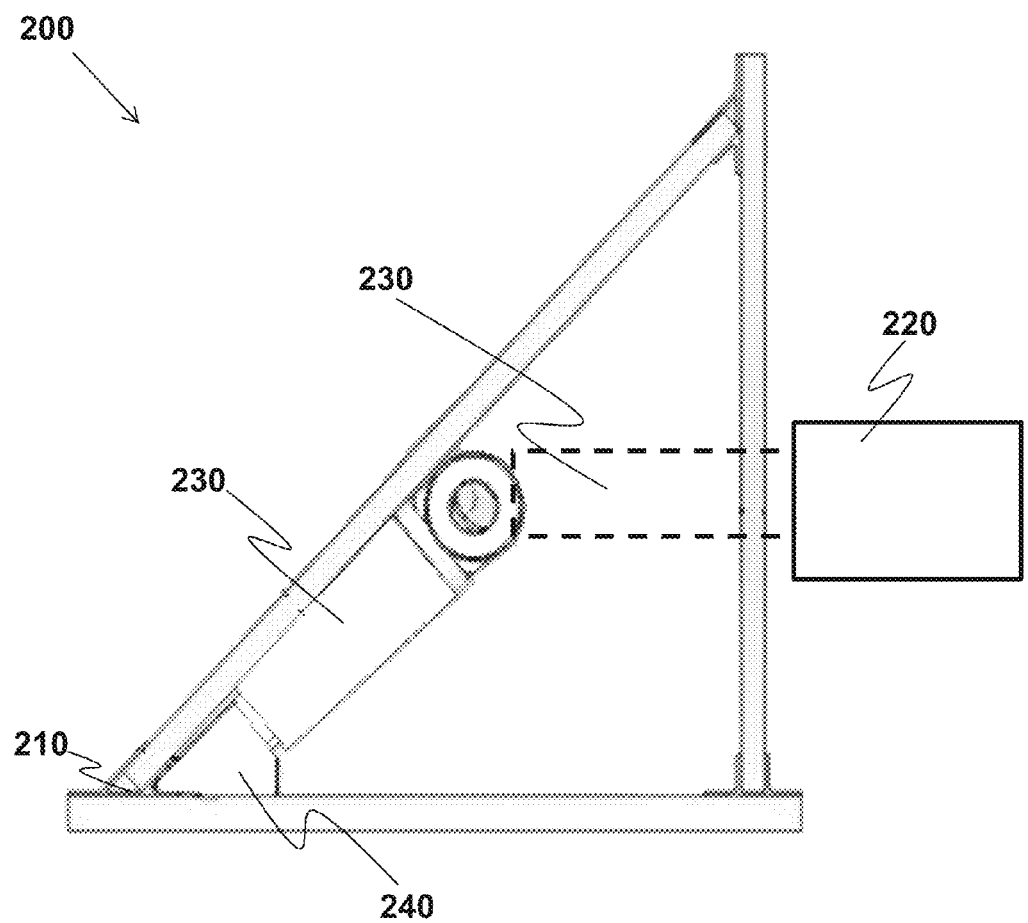
FIG. 2 illustrates an example arrangement of a laser bond inspection system in a confined area on an angled surface.

The embodiments claimed herein disclose using a compact surface motion sensor with an angled inspection head for LBI of an angled or compact, bonded article. With reference to FIG. 2, a system 200 for non-destructively inspecting a bond in an angled or compact bonded article 210 is provided, system 200 comprising: a laser 220; a laser beam delivery system 230; an angled inspection head 240; and a compact surface motion sensor 310 as depicted in and described herein with respect to FIG. 3.

In one embodiment, laser 220 may comprise, for example, a neodymium:phosphate glass laser, such as, for example, those manufactured by LSP Technologies, Inc., a YAG laser, a YLF laser, or any other solid-state crystal material, in either a rod or a slab gain medium. Laser 220 may be configured to deliver laser pulses having a pulse energy of between about 3 J and about 50 J (at the output of the final amplifier module), a wavelength of about 1054 nm, and a pulse width of between about 100 ns and 300 ns, and further being configured to deliver laser pulses in a low-high-low or probe-break-probe pulse energy sequence (i.e., a first laser pulse have a first energy, a second laser pulse having a second energy that is greater than the first energy but less than an energy required to break a properly constructed or "good" bond, and a third laser pulse having an energy which is approximately the same as the first pulse's energy), as described and illustrated in U.S. Pat. Nos. 7,770,454 and 8,156,811. In this sequence the low energy pulses interrogate the status of a bond line without significantly stressing the bond, the high energy laser pulse applied after the first low energy pulse applies a stress high enough to fail a weak bond but does no damage to a strong bond, and the lower energy pulse applied after the high energy laser pulse further interrogates the status of the bond line. By comparing the signals produced (using an EMAT sensor or optical interferometer) by a weak bond, a difference signal between the first low energy pulse and the third low energy pulse is recorded that allows a status of a bond line to be evaluated. Further configurations of laser 220 may include those described and illustrated in U.S. Pat. Nos. 7,770,454 and 8,156,811.

In one embodiment, laser beam delivery system 230 may comprise, for example, at least one of: (a) one or more mirrors; (b) an articulated arm; and (c) a fiber optic/optical fiber, and includes the laser beam delivery systems described and illustrated in U.S. Pat. Nos. 7,770,454 and 8,156,811. In one embodiment, where laser beam delivery system 230 is one or more mirrors, the beam may be directed to the surface of bonded article 210 without need for angled inspection head 240. In alternative embodiments, where laser beam delivery system 230 is an articulated arm and/or a fiber optic, laser beam delivery system 230 may be operatively connected to angled inspection head 240.

Figure 3:
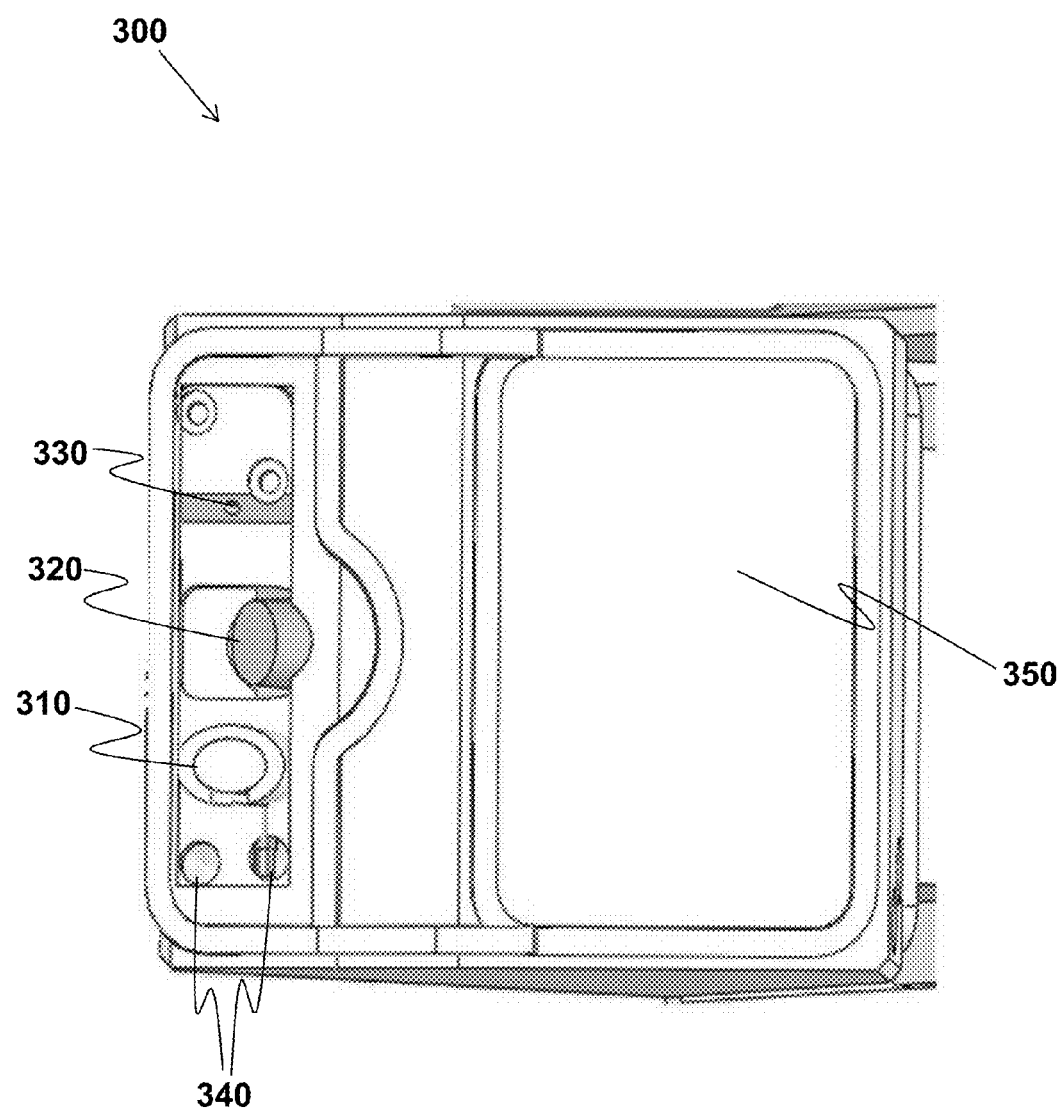
FIG. 3 illustrates an example angled laser inspection head with an off-axis EMAT compact surface motion sensor.

With reference to FIG. 3, angled inspection head 300 may comprise a laser inspection head similar to that disclosed in U.S. Pat. Nos. 7,770,454 and 8,156,811, except that inspection head 300 may be angled for LBI of angled, bonded structures and compact areas. A compact bonded article/ compact areas may include bonds in confined areas, that previously could not be accessed for LBI. An angled bonded article may include bonds with angles up to 50 degrees with respect to normal to a bonded article surface. Additionally, the on-axis EMAT sensor of the prior art may be replaced by one or more off-axis EMAT sensor(s) 310. To achieve inspection capability in composite structures with angled walls that are formed by pi joints, an LBI inspection head may be angled at up to about 50 degrees (with respect to normal to the part surface). The size and orientation of the on-axis EMAT sensor used in the inspection head disclosed in U.S. Pat. Nos. 7,770,454 and 8,156,811 may, in some configurations, prevent use of an angled head, and therefore it may be advantageous to replace the on-axis EMAT with an off-axis EMAT, e.g., off-axis EMAT 310. In one embodiment, off-axis EMAT 310 may be angled similar to angled inspection head 300. As shown, angled inspection head 300 also includes a laser beam output 320 to deliver a laser beam produced by a laser, e.g., laser 220, and communicated to output 320 via a laser beam delivery system, e.g., laser beam delivery system 230, accurately to a surface of an angled, bonded composite structure. A water nozzle 330 may be used to introduce a transparent overlay (e.g., water) for use in LBI. One or more transparent overlay evacuation port(s) 340 remove the transparent overlay after LBI is performed. An area for a vacuum attachment 350 or the like is provided to securely attach inspection head 300 to a part surface.

Figure 4:
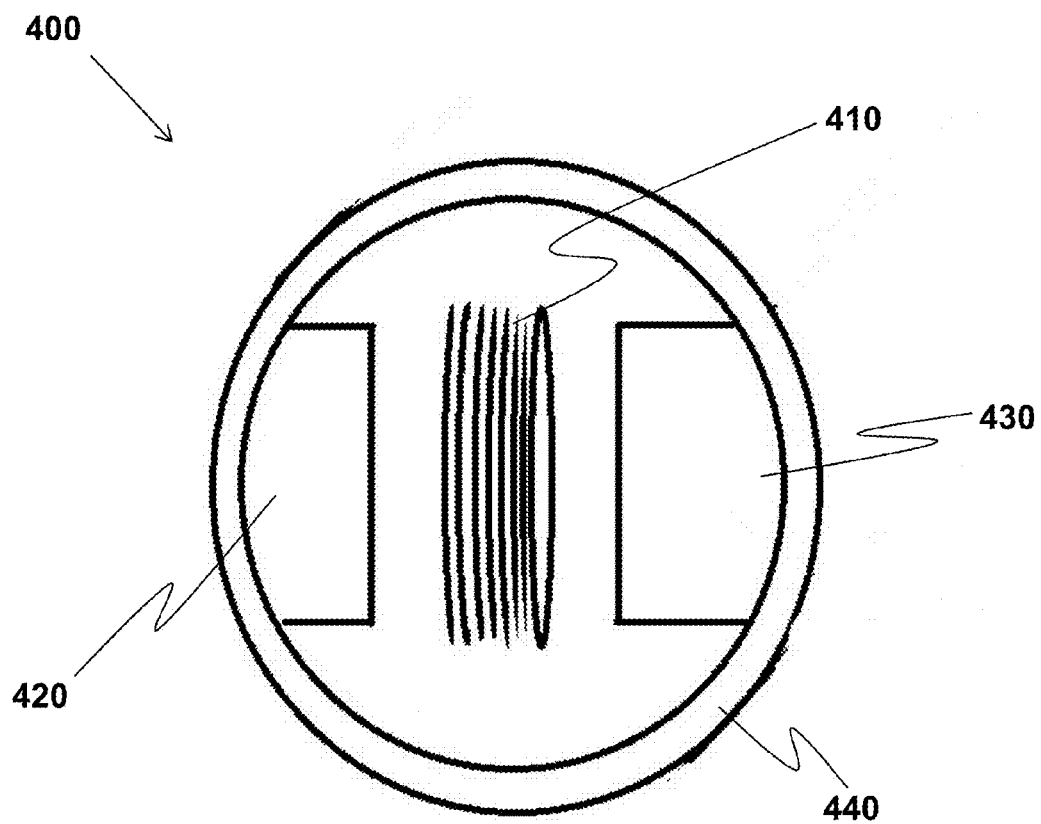
FIG. 4 illustrates a cross section of an off-axis EMAT compact surface motion sensor.

With reference to FIG. 4, a cross section of an off-axis EMAT sensor 400 is shown. One or more magnets 420 and 430 and a coil 410 are integrated in an off-axis EMAT sensor package 440. Because of this integration, off-axis EMAT sensor 400 may be produced in package 440 approximately ¼ inch in diameter and about ½ inch long, which is advantageously smaller than the prior art on-axis EMAT. Reduction in size of off-axis EMAT sensor 400 provides a significant cost savings, reduces the weight, and allows for a significantly smaller and an angled inspection head, e.g., angled inspection head 300, compared to the prior art. The change in configuration of off-axis EMAT sensor 400 produces an EMAT signal that is now representative of an off-axis stress wave (producing surface motion at a location off-axis from the laser beam impact area). In off-axis sensing, stress waves detected are not direct reflections over the disbanded area. Rather, the stress waves detected are reflections that have spread laterally and are characteristic of the disband. The size, weight, and cost reduction of off-axis EMAT sensor 400 allows for one or more EMAT sensors 400 to be placed on angled inspection head, e.g., angled inspection head 300, for improving signal strength and reliability. Another feature of an off-axis sensing approach may be the elimination of the requirement of precise alignment of inspection head to a conducting pattern. And, in some embodiments, a less expensive aluminum tape may replace a costlier custom inspection sticker (conducting pattern), thereby reducing the overall cost of LBI.

Off-axis EMAT sensor 400 may generally detect motion using magnets 420, 430 and coil 410 contained in package 440. Coil 410 may be parallel to the magnetic field lines produced by magnets 420, 430 and the bonded part surface. As stress waves cause a bonded surface to move perpendicular to the magnetic field lines produced by magnets 420, 430, a surface current may be induced and may flow perpendicular to the magnetic field lines and the surface motion. For non-conductive surfaces, aluminum tape may be used at a location of a sensor for producing a surface current. An induced surface current may induce a current in coil 410 of off-axis EMAT sensor 400. Coil current is measured by recording a voltage (EMAT signal) across a resistor in series with coil 410. Coil current is proportional to a part free-surface velocity as long as a time scale for changes in velocity is within a bandwidth of a coil characteristic response time. A determination of bond strength can be made by evaluating an EMAT signal. As discussed previously, use of multiple off-axis EMAT sensors 400 may provide an improved signature (i.e., EMAT signal) of a bond line condition. Any suitable algorithm may be employed to process EMAT signal for purposes of generating a data output including, but not limited to: a number, a graphical representation, or the like. In one embodiment, off-axis EMAT sensor 400 may be used to detect surface motion produced by LBI on a front surface of a bonded article. A front surface of a bonded article may be a surface on which a pulsed laser beam contacts a surface for laser interrogation of a bond in a bonded article.

Figure 5:
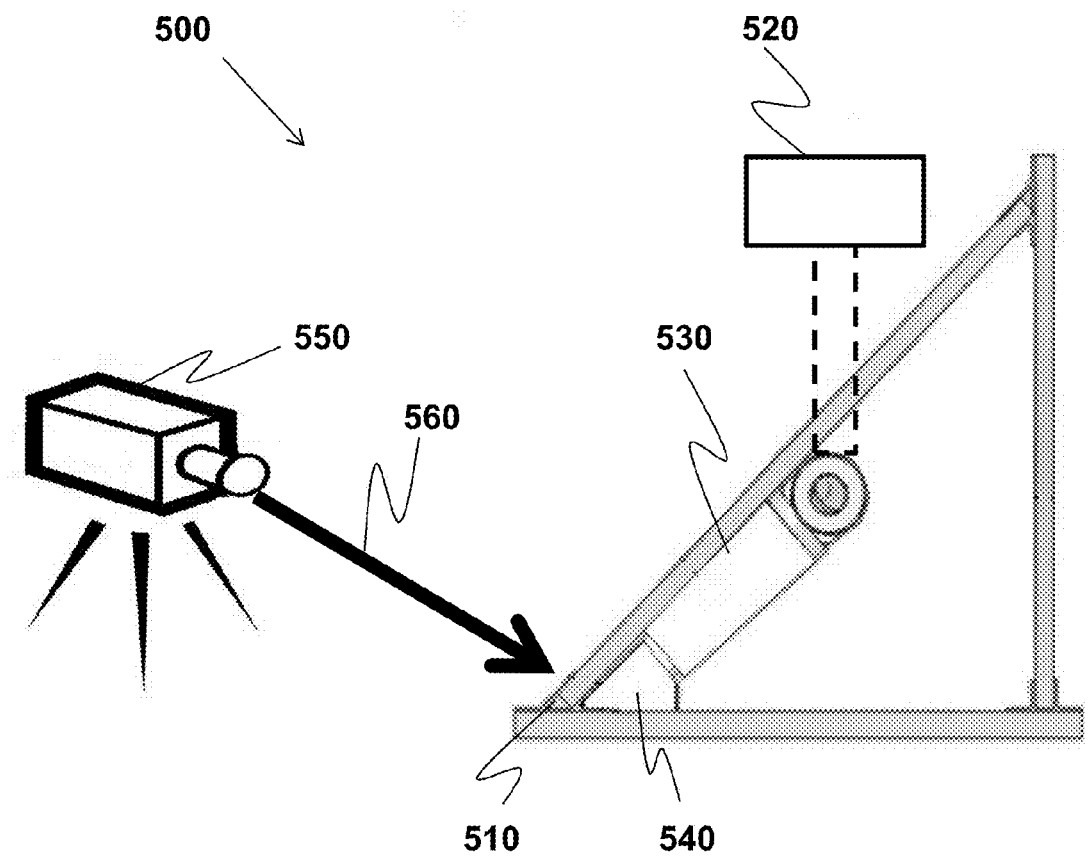
FIG. 5 illustrates an alternative embodiment of a laser bond inspection system using an optical interferometer to detect surface motion.

With reference to FIG. 5, an alternative embodiment system 500 for non-destructively inspecting a bond in an angled or compact bonded article 510 is provided, system 500 comprising: a laser 520; a laser beam delivery system 530; an angled inspection head 540; and an optical interferometer 550.

Optical interferometer 550 may be used with angled inspection head 540 to detect surface movement in a part during LBI. In one embodiment, optical interferometer 550 may be: an optical interferometer Model OVF-505 sensor head with Model OVF-5000 controller (with fiber delivery 560 of the sensing laser beam); a sensor head employing a HeNe laser and a modified Mach-Zehnder interferometer with heterodyne operation to sense velocity and displacement at a part surface during LBI; or signal from a sensor is decoded from a controller (VD-09 velocity decoder) and displacement (DD-300 displacement decoder). Of course, optical interferometer 550 is not limited to these embodiments. In one embodiment, a laser beam would be coupled into fiber 560 that would then be routed to the base of angled inspection head 540. Interferometer 550 may be remote from angled inspection head 540 as shown or may be integrated within angled inspection head 540.

Figure 6:
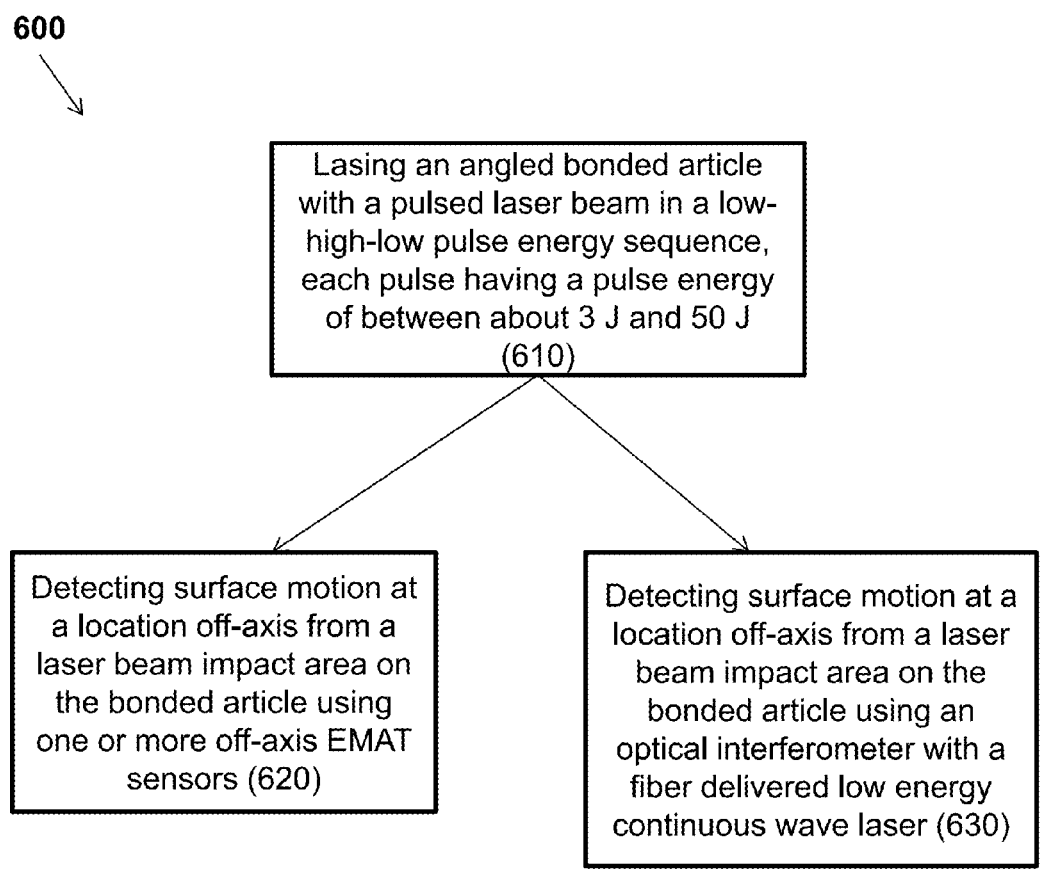
FIG. 6 is a flow chart of an example method for non-destructive testing of an angled composite bond in a bonded article.

Systems and apparatuses as described herein may be useful to non-destructively test an angled composite bond or a compact bonded article. FIG. 6 is a flow chart of a method 600 for non-destructive testing of an angled composite bond or a compact bonded article. In one embodiment, method 600 comprises: lasing an angled bonded article with a pulsed laser beam in a low-high-low pulse energy sequence, each pulse having a pulse energy of between about 3 J and about 50 J (610); and detecting surface motion at a location off-axis from a laser beam impact area on the bonded article using one or more off-axis EMAT sensors (620). In an alternative embodiment, step (620) may substituted with detecting surface motion at a location off-axis from a laser beam impact area on the bonded article using an optical interferometer with a fiber delivered low energy continuous wave laser (630). In one embodiment, steps (620) and (630) may be used interchangeably or together.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

As used in the specification and the claims, the singular forms "a," "an," and "the" include the plural. To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11.

What is claimed:

1. A system for laser bond inspection of a bond in an article, the system comprising:
    a laser to provide a pulsed laser beam;
    a laser beam delivery system to deliver the pulsed laser beam to an inspection head;
    the inspection head to deliver the pulsed laser beam to the article, wherein the inspection head is oriented at an acute angle with respect to normal to a surface of the article, wherein the inspection head comprises:
        a first output to generate a transparent overlay for the laser bond inspection of the bond in the article;
        a second output to deliver the pulsed laser beam to the surface of the article; and
        a surface motion sensor to detect surface motion in the article in response to delivering the pulsed laser beam to the surface of the article, wherein the surface motion sensor is further to generate one or more signals in response to detecting the surface motion.

2. The system of claim 1, wherein the laser is to provide a pulsed laser beam having:
    a pulse energy between about 3-50 Joules per pulse;
    a pulse width of about 70-300 nanoseconds (ns); and
    a beam diameter of about 5-12 millimeters (mm) at the surface of the bonded article; and
    wherein the laser is further to provide laser beam pulses in a low-high-low pulse energy sequence to cause stress waves through the bond of the article.

3. The system of claim 1, wherein the laser beam delivery system comprises one or more mirrors.

4. The system of claim 1, wherein the laser beam delivery system comprises an articulated arm attached to the inspection head.

5. The system of claim 1, wherein the laser beam delivery system comprises an optical fiber.

6. The system of claim 1, wherein the acute angle is one of about 50 degrees (°) and between 0° to 50 degrees relative to the normal to the surface of the article.

7. The system of claim 1, wherein the compact surface motion sensor comprises an off-axis electromagnetic acoustic transducer (EMAT) for detecting the surface motion at a location off-axis from a laser beam impact area associated with the pulsed laser beam.

8. The system of claim 1, wherein the surface motion sensor comprises an optical interferometer.

9. The system of claim 8, wherein the optical interferometer comprises an optical fiber to deliver a continuous wave laser to detect surface motion on the article.

10. A system comprising:
    a laser to provide a pulsed laser beam for laser bond inspection of a bond in an article;
    a laser beam delivery system to deliver the pulsed laser beam to an inspection head, wherein the inspection head comprises:
        a first output to generate a transparent overlay for the laser bond inspection of the bond in the article;
        a second output to deliver the pulsed laser beam to the surface of the article; and
        a surface motion sensor to detect surface motion in the article in response to delivering the pulsed laser beam to the surface of the article, wherein the surface motion sensor is further to generate one or more signals in response to detecting the surface motion.

11. The system of claim 10, wherein the inspection head is oriented at an acute angle with respect to normal to a surface of the article.

12. The system of claim 11, wherein generating the one or more signals in response to detecting the surface motion comprises generating one or more signals characterizing the detected surface motion.

13. The system of claim 12, wherein the acute angle is one of about 50 degrees (°) and between 0° to 50 degrees relative to the normal to the surface of the article.

14. The system of claim 13,
    wherein the article comprises a plurality of bonds; and
    wherein a given bond of the plurality of bonds is orientated at an acute bond angle with respect to the normal to the surface of the article; and
    wherein the inspection head is oriented relative to the normal to the surface of the article for laser bond inspection of the given bond in the article.

15. The system of claim 14, wherein the laser beam delivery system corresponds to one of an articulated arm and/or a fiber optic, and the inspection head corresponds to an angled inspection head.

16. The system of claim 13, wherein the acute bond angle is between 0° to 50 degrees relative to the normal to the surface of the article.

17. The system of claim 16, wherein the pulsed laser beam comprises:
    a pulse energy between about 3-50 Joules per pulse;
    a pulse width of about 70-300 nanoseconds (ns); and
    a beam diameter of about 5-12 millimeters (mm) at the surface of the article.

18. The system of claim 16, wherein the laser is further to provide laser beam pulses in a low-high-low pulse energy sequence to cause stress waves through the bond of the article.

* * * * *